US010247666B2

(12) United States Patent
Massie et al.

(10) Patent No.: US 10,247,666 B2
(45) Date of Patent: Apr. 2, 2019

(54) GAS DETECTION APPARATUS AND METHOD

(71) Applicant: Gas Measurement Instruments Limited, Scotland, Renfrewshire (GB)

(72) Inventors: Crawford Massie, Renfrewshire (GB); Fraser Mathieson, Scotland (GB); Andrew Glendinning, Scotland (GB)

(73) Assignee: Gas Measurement Instruments Limited (GB)

( * ) Notice: Subject to any disclaimer, the term of this patent is extended or adjusted under 35 U.S.C. 154(b) by 0 days.

(21) Appl. No.: 15/747,516

(22) PCT Filed: Jul. 27, 2016

(86) PCT No.: PCT/GB2016/052300
§ 371 (c)(1),
(2) Date: Jan. 25, 2018

(87) PCT Pub. No.: WO2017/017447
PCT Pub. Date: Feb. 2, 2017

(65) Prior Publication Data
US 2018/0217056 A1    Aug. 2, 2018

(30) Foreign Application Priority Data

Jul. 28, 2015   (GB) .................................. 1513313.5
Jan. 11, 2016   (WO) ................ PCT/GB2016/050055

(51) Int. Cl.
*G01N 21/00*     (2006.01)
*G01N 21/3518*   (2014.01)
(Continued)

(52) U.S. Cl.
CPC ........ *G01N 21/3518* (2013.01); *G01J 1/1626* (2013.01); *G01N 21/314* (2013.01);
(Continued)

(58) Field of Classification Search
CPC ........ G01J 1/16; G01J 1/1626; G01J 21/3504; G01N 21/3518; G01N 21/314;
(Continued)

(56) References Cited

U.S. PATENT DOCUMENTS 4,507,558 A    3/1985  Bonne
4,958,076 A    9/1990  Bonne et al.
(Continued)

FOREIGN PATENT DOCUMENTS

EP    1 947 454 A1    7/2008

OTHER PUBLICATIONS

International Search Report & Written Opinion of the International Searching Authority dated Nov. 18, 2016 issued in corresponding PCT Application Serial No. PCT/GB2016/052300, consisting of 10-pages.
(Continued)

*Primary Examiner* — Abdullahi Nur
(74) *Attorney, Agent, or Firm* — Christopher & Weisberg, P.A.

(57) ABSTRACT

A detector has a sensor responsive to a first wavelength, a sensor responsive to a second wavelength, and a sensor for collecting reference readings. A gas sample is analyzed to obtain readings corresponding to the first wavelength, the second wavelength and a reference. A first absorption figure is calculated using the first reading and the reference reading, and a second absorption figure using the second reading and the reference reading. A linearizer function is applied to the first and second absorption figures to calculate first and second concentration figures. The sensor for each wavelength is calibrated for detecting the first gas such that the data collected at each wavelength gives the same reading when only the first gas is present. The ratio of the first
(Continued)

concentration figure to the second concentration figure is used to identify whether only the first gas is present.

29 Claims, 11 Drawing Sheets

(51) Int. Cl.
*G01N 21/3504* (2014.01)
*G01N 21/31* (2006.01)
*G01J 1/16* (2006.01)
*G01N 33/00* (2006.01)

(52) U.S. Cl.
CPC .... *G01N 21/3504* (2013.01); *G01J 2001/161* (2013.01); *G01N 33/0059* (2013.01); *G01N 2021/3166* (2013.01); *G01N 2201/1215* (2013.01)

(58) Field of Classification Search
CPC ........ G01N 21/35; G01N 21/47; G01N 21/31; G01N 2201/10; G01N 2201/06
See application file for complete search history.

(56) References Cited

U.S. PATENT DOCUMENTS

| | | |
|---|---|---|
| 6,370,484 B1 | 4/2002 | Gorin et al. |
| 6,822,742 B1 | 11/2004 | Kalayeh et al. |
| 2002/0050567 A1 | 5/2002 | Boudet et al. |
| 2004/0036023 A1 | 2/2004 | Hodgkinson |
| 2011/0112386 A1* | 5/2011 | Maki ................. A61B 5/14532 600/322 |

OTHER PUBLICATIONS

International Search Report & Written Opinion of the International Searching Authority dated May 2, 2016 issued in corresponding PCT Application Serial No. PCT/GB2016/050055, consisting of 11-pages.

* cited by examiner

GAS DETECTION APPARATUS AND METHOD

CROSS-REFERENCE TO RELATED APPLICATIONS

This Application is a Submission Under 35 U.S.C. § 371 for a U.S. National Stage Patent Application of International Application Number PCT/GB2016/052300, filed Jul. 27, 2016 entitled "GAS DETECTION APPARATUS AND METHOD." This Application and International Application Number PCT/GB2016/052300 are related to and claim priority to International Application Number PCT/GB2016/050055, filed Jan. 11, 2016 entitled "GAS DETECTION APPARATUS AND METHOD, all of which are related to and claim priority to GB1513313.5 filed Jul. 28, 2015, entitled "GAS DETECTION APPARATUS AND METHOD." The entireties of all of PCT/GB2016/050055, PCT/GB2016/052300 and GB1513313.5 are incorporated herein by reference.

The present invention relates to gas detection apparatus and more particularly to apparatus for distinguishing between different types of gas.

Apparatus and methods are known in the art for detecting the presence of gas within an environment and also for discerning the composition of the gas mixture. Many such processes and equipment is lab based, but in many applications the delay associated with collecting a gas sample and sending it to a lab for analysis is undesirable or unacceptable. For example gas utilities concerned with the distribution of natural gas must act promptly to any report of a gas leak from a gas supply line. A majority of the gas distribution pipe work is subterranean, and there is, therefore, significant cost associated with excavating pipework, which may be under roads etc. It can, however, be the case that the gas which has been reported is not, in fact, leaking from a pipeline but from some other source. Natural gas is a mixture of hydrocarbons such as methane, ethane, propane, butane, etc. However, basic detectors will also respond to other sources of gas, such as landfill gas, which is primarily methane. In order, then, to avoid un-necessary excavation, there is a need for a system for distinguishing between different types of gas prior to digging.

As already mentioned above, lab based equipment is known in the art which can analyse a gas sample and distinguish between different gas types/identify components. However, collecting a sample and sending for lab analysis would incur significant delay and, depending on the severity of the leak may not be an option.

One known solution is to provide a miniature gas chromatograph in a portable gas detection instrument. This instrument collects a sample of gas and, over a period of several minutes, provides an indication of the make-up of the gas.

Another approach known in the art has been to use a laser based detector. Whilst these work very effectively, they are prohibitively expensive.

U.S. Pat. No. 4,958,076 discloses a selective gas detecting apparatus which can be used to determine the concentration and type of hydrocarbon gas in a gas sample. It does this by use of at least two infrared radiation absorption channels each responsive to a different wavelength, in particular 3.2 microns and 3.4 microns. The infrared absorption channels work by measuring the amount of infrared radiation absorbed by the gas sample at the particular wavelength. The data from each channel on its own will give an indication of the concentration of the particular hydrocarbon to which it is tuned but is also sensitive to other hydrocarbons. In US'076, the absorption data from each channel is used to calculate an absorbance figure for each channel and the ratio of the absorbance figures for the two channels is then used to infer the type of hydrocarbon present. In order to minimise the effect of variances in output of different sensors tuned to the same wavelength, US'076 further proposes taking the logarithm of the ratio of the output of the pair channels since this will reduce the impact of any such variance. This was an acceptable approach when using analogue systems of the type taught in US '076 but is less acceptable with more accurate digital systems which are now more commonly utilised.

There is accordingly a need for an improved gas detecting system which is able to provide more accurate information regarding both the identification of the gas present in a sample as well as information regarding the concentration of that gas. It is a further aim of the invention to provide such a system which reduces the effect of variations in composition on the measurement readings. It is still further a need that such a system be implementable in a portable apparatus so as to enable rapid analysis to be carried out at the site of a suspected gas leak.

According to a first aspect of the present invention there is provided a method of identifying the presence of a first gas within a sample, comprising the steps of providing a detector having a sensor responsive to a first wavelength, a sensor responsive to a second wavelength, and a sensor for collecting reference readings; analysing a gas sample to obtain a first absorption reading corresponding to the first wavelength, a second absorption reading corresponding to the second wavelength and a reference reading; calculating a first absorption figure using the first absorption reading and the reference reading, and a second absorption figure using the second absorption reading and the reference reading; applying a lineariser function to each of the first and second absorption figures to calculate first and second concentration figures; calibrating the sensor for each wavelength for detecting the first gas such that the data collected at each wavelength gives the same reading when only said first gas is present in a sample; calculating the ratio of the first concentration figure to the second concentration figure, and using said ratio to identify whether only the first gas is present in the sample.

The method of the first aspect of the present invention differs from the prior art in that the sensor for each wavelength is calibrated for detecting the first gas so that they give the same reading if only the first gas is present in a sample. Furthermore, in the method of the present invention, the reading for each wavelength is first processed using a lineariser function to calculate a concentration reading, the two concentration readings then being used to calculate a ratio. This compared with the prior art where the absorption figures for each channel are each processed using logarithm function to produce absorbance figures, which are then divided by each other to produce a figure for the ratio of the two absorbance figures.

The method according to the first aspect of the invention thereby has the advantage that, by applying a lineariser function to the readings and then calculating the ratio of the concentrations, the ratio figure obtained is not susceptible to sensor variations such as variance in filters in the sensors due to manufacturing tolerances. As a result, a more reliable identification can be made.

The present invention is particularly useful in distinguishing between methane and higher hydrocarbons such as propane and butane and is particularly useful for distinguishing methane from natural gas. Preferably, then, the first wavelength is 3.3 microns plus or minus 0.1 microns and the second wavelength is 3.4 microns plus or minus 0.1 microns. Calibration is then carried out for detecting methane such that the same reading is obtained at each wavelength when analysing a sample containing methane but no other hydrocarbons. In that case, the ratio figure calculated according to the invention will be 1, so that calculation of a ratio of 1 is indicative of methane being in the sample.

Natural gas includes a range of hydrocarbons which includes methane as well as many others. Due to their differing operating wavelengths, when a sample containing natural gas is analysed by the sensors, the readings from the two sensors will be different, and the difference between the two readings will increase with increasing concentrations of the natural gas. Accordingly, calculation of a ratio of greater than 1 is indicative of gas other than methane being present in the sample. The way in which the sensor is calibrated with methane means that it will indicate that the gas is not methane if the gas sampled is either, say, natural gas or any of the higher hydrocarbons.

Preferably, compensation is carried out separately on the reading at each wavelength in order to eliminate errors due to variations in environmental parameters. In particular at least one of temperature compensation and pressure compensation may be carried out, with temperature compensation preferably being carried out in two stages—zero drift correction and span drift correction.

When utilising sensors of the type used in the present invention which are both calibrated for detecting the same first gas (preferably methane), when the sample measured is actually the second gas (preferably natural gas), or any other hydrocarbon, the increased absorption relative to the first gas means that the reading given will be higher than the actual concentration. In the case of natural gas, where volume levels are present, the concentration indicated by the lineariser can be hundreds of percent above the actual concentration.

There is, accordingly, a need for compensating for the increased absorption so as to enable a more accurate value for the actual concentration of the gas in the sample to be obtained from the readings taken from the sensors.

Preferably, two sensors are used, one for each wavelength. However, a single sensor operable in different modes, such as with a variable or changeable filter, to allow it to take readings at different wavelengths, either simultaneously or at different times may also be utilised within the scope of the invention, the important feature being that data can be collected from the same sample corresponding to the two different wavelengths.

The or each sensor may be an infrared radiation absorption sensor, in particular a broadband IR source (such as, for example, a flashing incandescent bulb) together with suitable spectral filter(s) and detector(s) applicable for the required wavelength. However, the sensor may instead incorporate an emitter which emits light at the required wavelength, thereby avoiding the need to use the source in conjunction with filters. In particular, LED's which emit light at the first and second wavelengths may be utilised, or possibly an LED which is operable in two modes corresponding to the first and second wavelengths.

In accordance with another aspect of the present invention there is provided a method of measuring the concentration of either a first gas in a sample, comprising the steps of providing a detector having a sensor responsive to a first wavelength, a sensor responsive to a second wavelength, and a sensor for taking reference readings; applying a lineariser function to each of the first and second absorption figures to calculate first and second concentration figures, calibrating the sensor for each wavelength for detecting the first gas such that the data at each wavelength gives the same reading when only said first gas is present in a sample; analysing a gas sample to obtain a first absorption reading at the first wavelength, a second absorption reading at the second wavelength and a reference reading; calculating a first concentration figure ($c_1$) and a second concentration figure ($c_2$) using the reading at the first wavelength, the reading at the second wavelength and the reference reading, and calculating a corrected concentration figure ($c_{cor}$) indicative of the actual concentration of said one of the first gas and the second gas in the sample using the equation $c_{cor}=c_1-X\cdot(c_2-c_1)$, in which $X=A\cdot(c_1/c_2)^B$, where A and B are constants for a particular pair of filter wavelengths chosen depending on the gases which are being looked for in the sample.

The method according to the second aspect of the invention has the advantage of providing correction for errors in the concentration readings arising from the differential readings at the two wavelengths due to the different gases looked for in the sample.

Preferably, the first gas is methane and its concentration is being measured in a sample containing natural gas or another higher hydrocarbon, in which case $A=2.5577$ and $B=1.869$. The values of A and B will, however, be different for different values of the first and second wavelengths (these may be different if, for example, the method is being used in association with other gases). In that case, values for A and B can be calculated empirically as set out below.

Although this correction is found to produce values which are significantly more accurate that prior art approached which did not utilise this correction method, it has been found that the correction algorithm does introduce noise to the measurement when only methane is present. Preferably, therefore, if the gas present is methane, the algorithm is not used and instead the output of the first sensor only is used to calculate the concentration reading.

In a particularly preferred embodiment, the equation is used only where the ratio of the reading of the first sensor to the second sensor ($c_1/c_2$) is above a first threshold value, the output of the first sensor only is used where ($c_1/c_2$) is below a second threshold value, and a transitioning algorithm is used where ($c_1/c_2$) is between the first and second threshold values.

In particular, the first threshold valve is 1, and the second threshold value is 0.9. In that case, the correction equation utilised is $c_{cor}=M2\cdot(c_1-X\cdot(c_2-c_1))+M1\cdot c_1$, where $M1=(z-0.9)/(1-0.9)$, and $M2=(1-z)/(1-0.9)$, with $z=0.9$ when ($c_1/c_2$)<0.9, $z=1$ when ($c_1/c_2$)>1, and $z=(c_1/c_2)$ when $0.9\leq(c_1/c_2)\leq 1$.

This has the advantage of removing the effect of noise introduced by the correction algorithm by not using it when the basic readings from the sensors indicate that the concentration is within the noisy range, i.e. by not using the algorithm when only methane is present.

In a further development of the method of the second aspect of the invention, it has been found that the accuracy of the corrected concentration value can be improved by introducing a correction factor into the equation which depends on the measured value of the concentration taken from the first sensor D1.

Accordingly, the present invention further provides a method of measuring the concentration of a first gas in a sample, comprising the steps of providing a detector having a sensor responsive to a first wavelength, a sensor responsive to a second wavelength, and a sensor for taking reference readings; applying a lineariser function to each of the first and second absorption figures to calculate first and second concentration figures, calibrating the sensor for each wavelength for detecting the first gas such that the data at each wavelength gives the same reading when only said first gas is present in a sample; analysing a gas sample to obtain a first absorption reading at the first wavelength, a second absorption reading at the second wavelength and a reference reading; calculating a first concentration figure ($c_1$) and a second concentration figure ($c_2$) using the reading at the first wavelength, the reading at the second wavelength and the reference reading, and calculating a corrected concentration figure ($c_{cor}$) indicative of the actual concentration of said first gas in the sample using the equation $c_{cor}=c_1-X\cdot(c_2-c_1)$, in which $X=D\cdot A\cdot(c_1/c_2)^B$, where A and B are constants for a particular pair of filter wavelengths chosen depending on the gases which are being looked for in the sample, and D is a correction factor which depends on concentration of the first gas in the sample.

Preferably, the value of D is extrapolated from calibration readings taken using the detector to measure the concentration of a first gas mixture of known composition at least at two known concentrations, and of a second gas mixture of a known composition which is different to the composition of the first gas mixture at least at two known concentrations, the calibration readings preferably being taken using the same concentration values for each of the first and second gas mixtures, and in particular the readings being taken at 100% of the each gas mixture, and at 50% of each gas mixture in nitrogen.

The calibration values of D are preferably calculated using readings taken from sample of known composition using the equation $$D = \frac{C_1 - C_{cor}}{A \cdot \left(\frac{C_1}{C_2}\right)^B (C_2 - C_1)}$$

where $C_1$ and $C_2$ are the sensor readings take for the sample and $C_{cor}$ is the actual concentration of the gas in the known sample. The value of D for a sample of unknown composition is then preferably extrapolated from the calibration values of D using a linear extrapolation between the calibration values to extrapolate to a value of D for the measured value of C1 for the sample.

In a particularly preferred embodiment, D is calculated for a particular sample of unknown composition using the equation:

$$D = NG1_{cor} \cdot D_{NG1}(c_1) + NG2_{cor} \cdot D_{NG2}(c_1)$$

where $$NG1_{cor} = \frac{R_{@100\%NG2} - R}{R_{@100\%NG2} - R_{@100\%NG1}}$$

and $$NG2_{cor} = \frac{R - R_{@100\%NG1}}{R_{@100\%NG2} - R_{@100\%NG1}}$$

With $R=C_2/C_1$; $R_{@100\%\ NG1}$=calibration Determination ratio measured at the at least one known concentration of the first gas mixture of known composition NG1, $R_{@100\%\ NG2}$=calibration Determination ratio measured at the at least one known concentration of the second gas mixture of known composition NG2, and $D_{NG1}$ is the linear equation which extrapolates between the calibrations values of D for the first gas mixture and $D_{NG2}$ is the linear equation which extrapolates between the calibrations values of D for the second gas mixture.

The method according this third aspect of the invention may also be utilised with the preferable options set out above and below in connection with the second aspect of the invention.

In a particularly preferred embodiment of the present invention the correction algorithm of the second or third aspect of the invention is utilised in combination with the identification method according to the first aspect of the invention.

Again, although in the preferred embodiment a separate sensor is used for each wavelength, a single sensor configured to collect data at the three different wavelengths (including the reference readings) may also be used.

The present invention further provides a selective gas detecting apparatus comprising a sensor responsive to a first wavelength, a sensor responsive to a second wavelength, and a sensor for collecting reference readings; and processing means, said processing means being programmed to calculate a first absorption figure using the reading for the first wavelength and the reference reading, and a second absorption figure using the reading for the second wavelength and the reference reading; to calculate first and second concentration figures by applying a lineariser function to each of the first and second absorption readings; the sensor for each wavelength being calibrated for detecting the first gas such that the reading for each wavelength is the same when only said first gas is present in a sample; to calculate the ratio of the first concentration figure to the second concentration figure, and to identify the gas which is present in the sample based on the calculated ratio.

The present invention still further provides a selective gas detecting apparatus comprising a sensor responsive to a first wavelength, a sensor responsive to a second wavelength, and a sensor for collecting reference readings; the sensor for each wavelength being calibrated for detecting a first gas such that the reading for each wavelength is the same when only said first gas is present in a sample; and processing means, said processing means being programmed to apply the method according to the second aspect of the invention.

Preferably a separate sensor is used for each of the first wavelength, the second wavelength and the reference reading.

For each of the above aspects of the invention, the or each sensor may be an infrared radiation absorption, in particular a broadband IR source (such as, for example, a flashing incandescent bulb) used together with suitable spectral filter(s) and detector(s) applicable for the required wavelength. However, the sensor may instead incorporate an emitter which emits light at the required wavelength, thereby avoiding the need to use the source in conjunction with filters. In particular, LED's which emit light at the first, second and reference wavelengths may be utilised, or possibly a single LED which is operable in three modes corresponding to the first, second and reference wavelengths.

In order that the invention may be well understood, there will now be described some embodiments thereof, given by way of example, reference being made to the accompanying drawings, in which.

Figure 13:
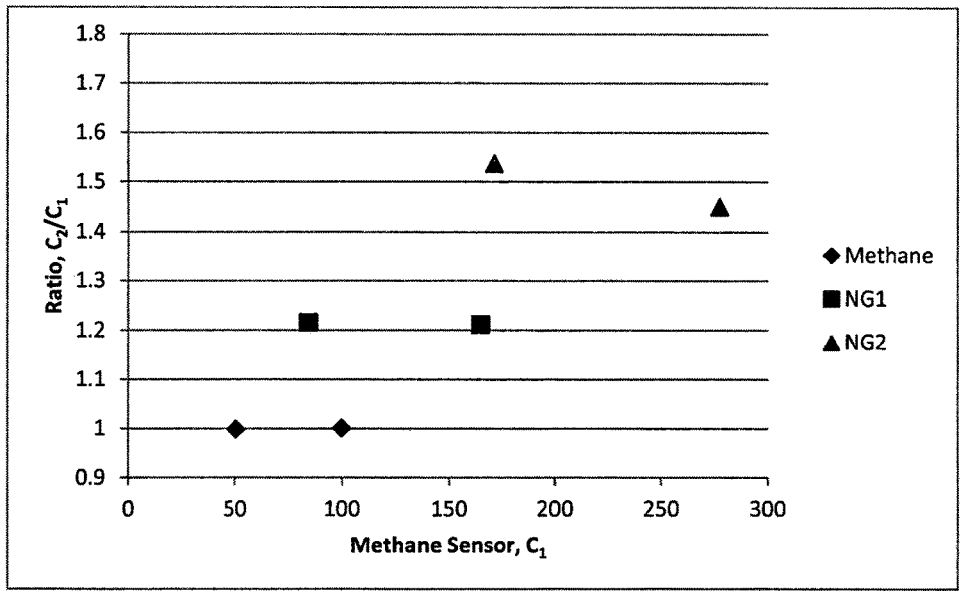
Figure 14:
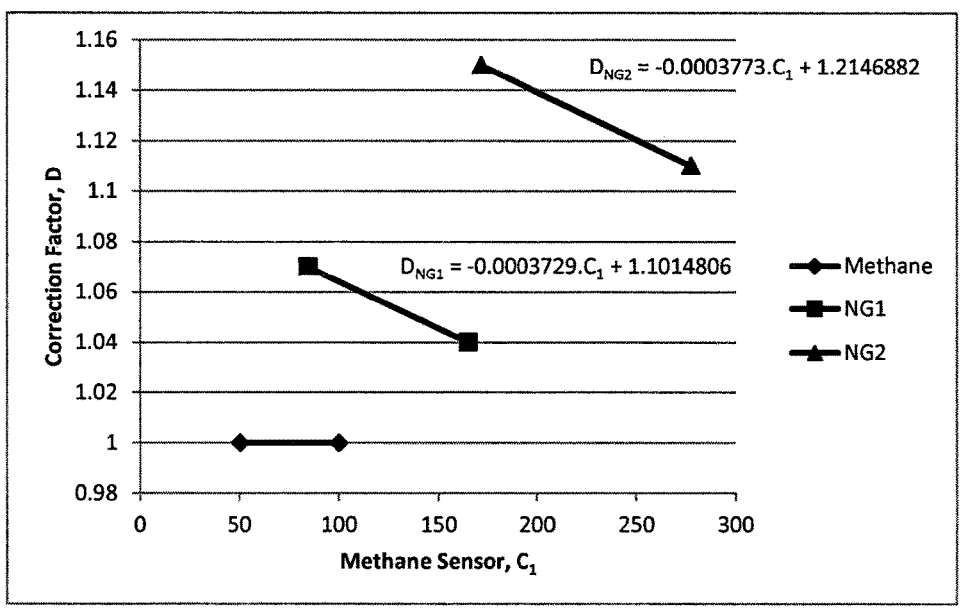

FIG. 13 is a graph showing calibration reading of a methane sensor plotted against the ratio of the output of the methane sensor to the output of another hrydocarbon sensor taken on a number of samples of known but different composition and concentration; and FIG. 14 is a graph showing the output of the methane sensor plotted against value of a correction factor calculated from the calibration data shown in FIG. 13.

NDIR spectroscopic detection of methane is a widely used technique with sensors being available from various suppliers. However there are no sensors of this type that have been used successfully to identify natural gas. Such sensors can, be spec'd to measure different parts of the IR spectrum, so as to produce a sensor where the target gas is methane or a sensor where the target gas is the higher hydrocarbons (propane, butane, etc). Regardless though, of the target gas, they will still respond to all hydrocarbons to different degrees.

The preferred embodiment of the present invention now described is based on provision of a detector which has a methane sensor and a hydrocarbon sensor. Although the detailed description of the invention relates refers to methane and hydrocarbon, it will be understood that this is for illustration purposes only and that the invention is applicable to gases in general and is not necessarily limited only to detection of methane.

Accordingly, the detector utilised as part of the present invention effectively has two hydrocarbon sensors. They both respond to hydrocarbons, but to different degrees. If both are calibrated for methane, and methane is the only gas present, both will produce the same result. However, if another hydrocarbon is present as well as methane, e.g. ethane as will be the case for natural gas, the two sensors will produce different results. This unbalancing of the signals in the presence of natural gas is what enables the discrimination between methane and natural gas in the present invention.

The sensors utilised in the invention are Non-dispersive IR sensors, which use the basic principles of Infrared spectroscopy to measure the concentration of gas. Put simply, the gas absorbs light at specific wavelengths (spectroscopic fingerprint). The amount of light absorbed will depend on the concentration of the target gas, the higher the concentration, the greater the absorption.

This process can be modelled by the Beer-Lambert equation, $$I = I_0 e^{-\alpha c l} \quad (1)$$

Where $I_0$=Light intensity in air; $\alpha$=absorption coefficient; c=gas concentration; and l=optical pathlength.

Because a non-dispersive system looks at a many number of absorption lines and not just at a single line of the gas (as in laser spectroscopy), the product '$\alpha l$' is not constant, but is dependent c.

The sensor used in the preferred embodiment of the invention consists of three pyroelectric detectors and an infrared source. The three detectors each have a spectral filter for detecting different parts of the mid-IR spectrum.

In the invention, the specifications of the three filters are as follows:

Filter 1 (methane): 3.33 um+/−0.1 um
Filter 2 (higher hydrocarbons): 3.40 um+/−0.1 um
Filter 3 (reference): 3.95 um+/−0.1 um The bandwidth of each filter is in the order or hundreds of nanometers, such as, for example, 160 nm for Filter 1, 120 nm for Filter 2, and 90 nm for Filter 3. These bandwidths values are not, however exclusive, and will vary depending on the specification of the sensors used.

The infrared source is flashed at 4 Hz. This generates a 4 Hz sinusoidal waveform at the output of the detector circuitry, the amplitude of which is measured to provide an indication of the amount of light arriving at the detector ('I' in equation 1)

The method by which natural gas is identified is as follows:

First the absorption in each channel is calculated (using the reference detector as a measure of the signal strength in air).

$$abs_m = 1 - \frac{I_m}{I_r} \quad (2)$$

$$abs_{hc} = 1 - \frac{I_{hc}}{I_r} \quad (3)$$

Where,
$I_m$=normalised methane channel intensity;
$I_{hc}$=normalised hydrocarbon channel intensity;
$I_r$=normalised reference channel intensity;

A lineariser equation is then used to calculate the concentration measured in each channel.

$$c = c(abs) \quad (4)$$

Where c(abs)=lineariser function.

There is a separate lineariser for each channel.

The ratio of the two calculated concentrations is then calculated, $$R = \frac{c_{hc}}{c_m} \quad (5)$$

If R=1, the gas is methane.

Due to the position of the spectral filters and the relative strengths of absorption for methane and the other hydrocarbons, the hydrocarbon channel will see a greater absorption than the methane channel in the presence of natural gas (or any hydrocarbons other than methane). This means for natural gas $C_2 > C_1$. Therefore, if R>1 it can be deduced that the gas is not solely methane.

The gas determination ratio, equation 5, is in theory quite straight forward. However, because the ratio of two numbers is being taken, if these numbers are small, as in the case for low gas concentrations, it has been found that noise can play a significant part in the calculation. It has also been found to be desirable to account for errors in linearity. So, in the preferred embodiment, limits are to be set to reduce the chances of an incorrect determination.

The preferred limits are:

If $C_1 < Y$, then gas is undermined; (Signals are too low to make a reliable decision)

If $C_1 > Y$ AND R<1.025, then gas is methane;

If $C_1 > Y$ AND 1.025<R<1.05, then gas is undetermined; (this is a buffer to take into account noise and sensor to sensor variation in linearity)

Figure 1:
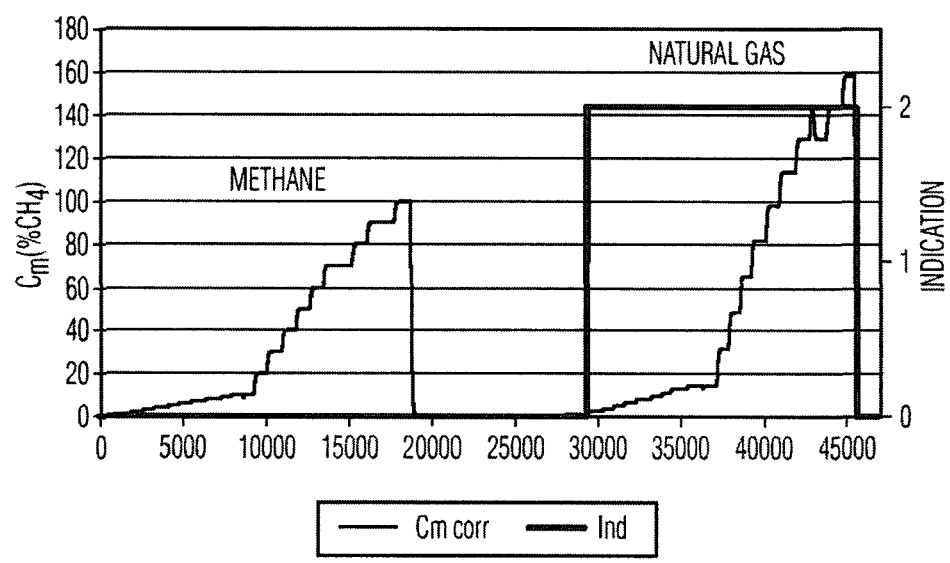
FIG. 1 is a graph showing an example of indication algorithm for a sensor according to a preferred embodiment of the invention with methane and natural gas.

If $C_1 > Y$ AND R>1.05, then gas is natural gas;

where Y is constant which is selected to provide acceptable results depending on the particular calibration value etc. The lower the value of Y the greater the sensitivity of the system but all the more susceptible it is to noise. Preferably, Y is less than or equal to 1.5, and more particularly is equal to 1.0, especially for calibration at 1% concentration of methane. An example of the indication algorithm working is shown in FIG. 1.

It is well known to apply environmental compensation to compensate for changes in sensor output with environmental conditions such as temperature and pressure.

For the preferred embodiment of the invention, temperature compensation of the sensors has to be done separately for each absorption channel. It also needs to be done in two stages.

1. Zero drift correction
2. Span drift correction

Data should be compared for a larger number of sensors (circa 100) in order to check how similar/different the sensors were from each other after the lineariser is applied.

Figure 2:
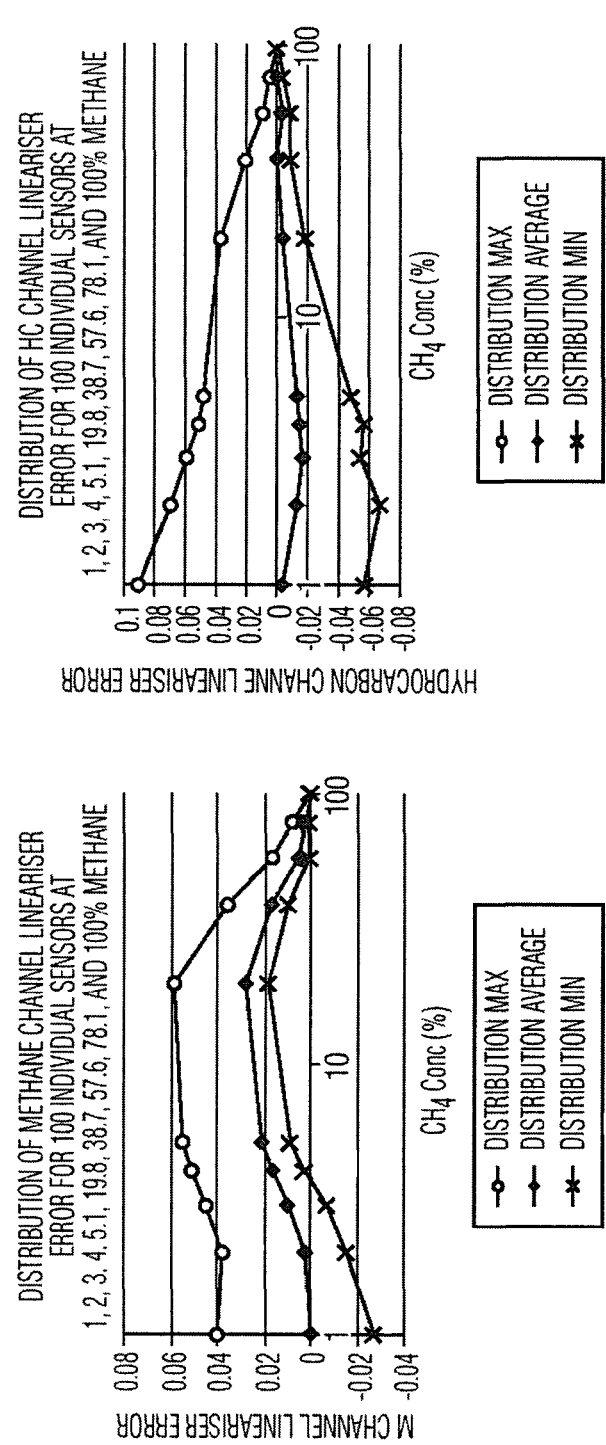
FIG. 2 is a graph showing the distribution of lineariser error for a sample batch of the methane and hydrocarbon sensors.
Figure 3:
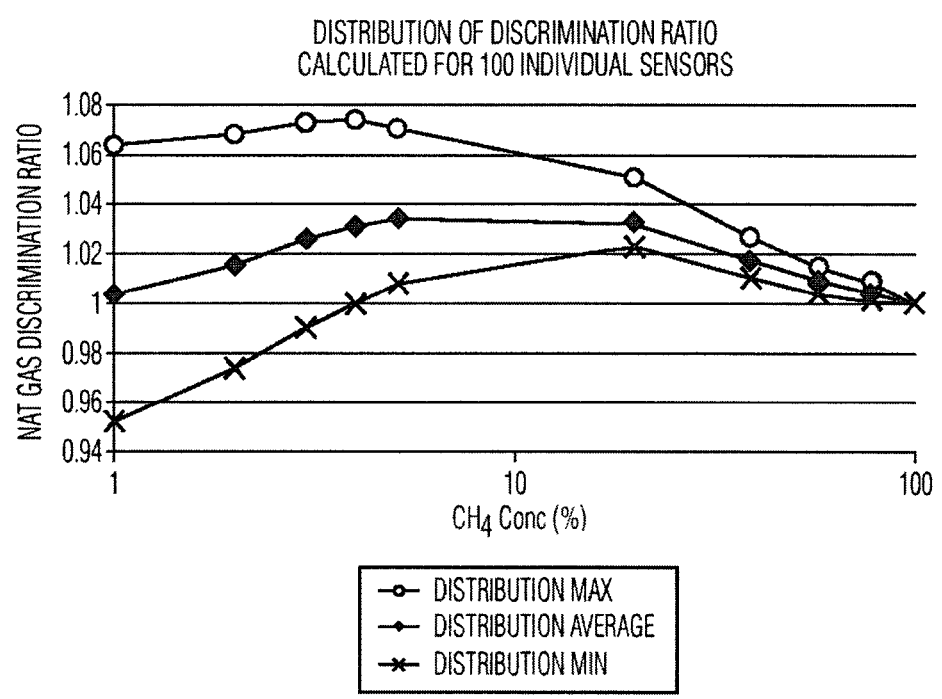
FIG. 3 is a graph showing the variations in gas determination ratio for different sensor batches.

Although small errors in linearity, shown in FIG. 2, are not that concerning in themselves for calculation of the gas concentration, they can feed through to significant errors when calculating the gas determination ratio as shown in FIG. 3.

FIG. 3 shows that for a batch of 100 examples of the preferred embodiment, many of the data points measured lie in the undetermined region of 1.025<R<1.05. There are also a few errors where R>1.05, which would give an indication of natural gas, when the gas is actually methane.

To improve the scenario in FIG. 3, a method has been created whereby the sensors are calibrated at 1% and 5% methane, as well as 100% methane.

The equations for correction of the linearized data are:

0-5% Methane:
$$c_{corr} = c - c \cdot Err_{1\%} \cdot \left(\frac{5-c}{4}\right) - c \cdot Err_{5\%} \cdot \left(\frac{c-1}{4}\right) \quad (13)$$

5-100% Methane:
$$c_{corr} = c - c \cdot Err_{5\%} \cdot \left(\frac{100-c}{95}\right) \quad (14)$$

Where, $$Err_{1\%} = \frac{c_{1\%} - 1}{1} \quad (15)$$

$$Err_{5\%} = \frac{c_{5\%} - 5}{5} \quad (16)$$

Figure 4:
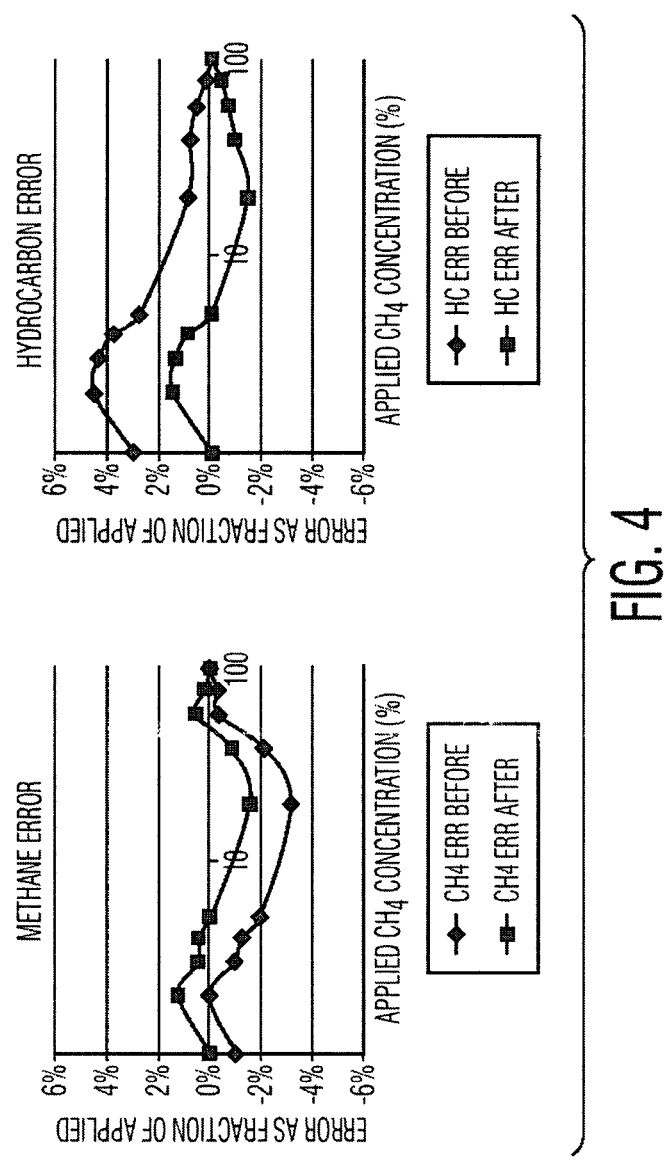
FIG. 4 are graphs showing the effects of correction according to the invention on both methane and hydrocarbon sensor data.
Figure 5:
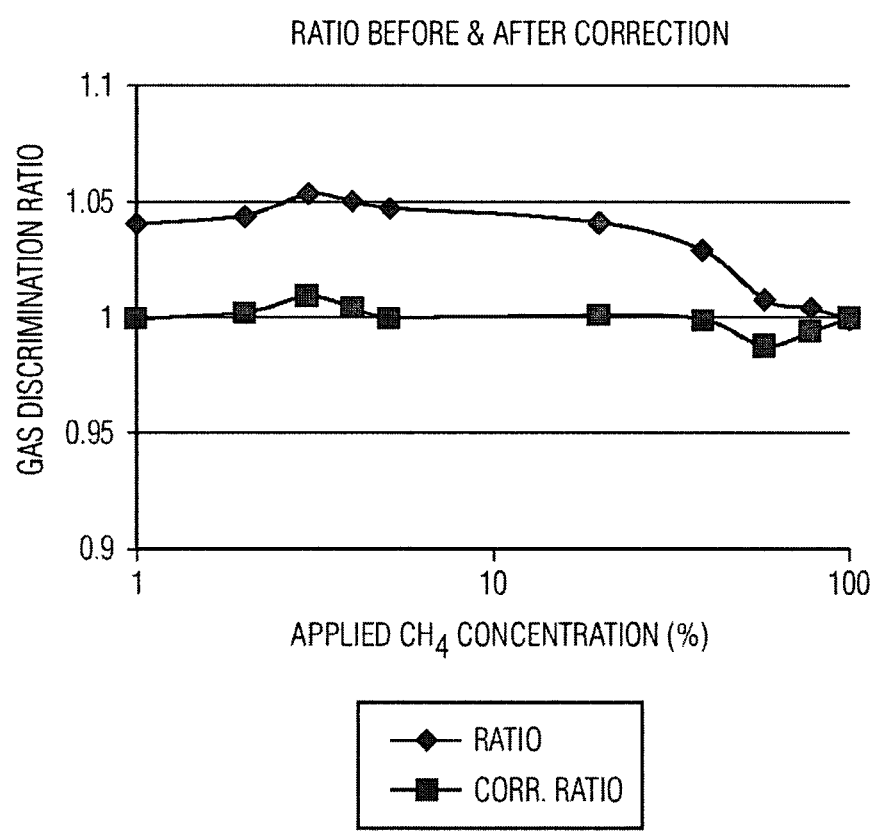
FIG. 5 is a graph showing the effect of applying the lineariser correction algorithm of the invention on the gas determination ratio.

$c_{1\%}$ and $c_{5\%}$ are the lineariser outputs for 1% and 5% methane before correction. The results of this correction algorithm are shown in FIG. 4 and FIG. 5.

For the particular sensor of the example, a mainly 'undetermined' decision is produced before correction. Following the correction a marked improvement in calculation of the Gas Discrimination Ratio is achieved, and can be corrected across the full range. This three point calibration need only be a one off event at initial calibration, and serve as a way to characterise each individual sensor. Subsequent calibrations should only need to be done at 100% methane.

Because the linearisers used in the instrument according to the method of the preferred embodiment of the invention are calibrated for methane, if the instrument measures natural gas, or any of the other hydrocarbons, the increased absorption relative to methane mean it will read high. In the case of volume levels of natural gas, the concentration indicated by the lineariser can be hundreds of percent above the actual concentration present. Examples of this are shown in FIG. 6.

Figure 7:
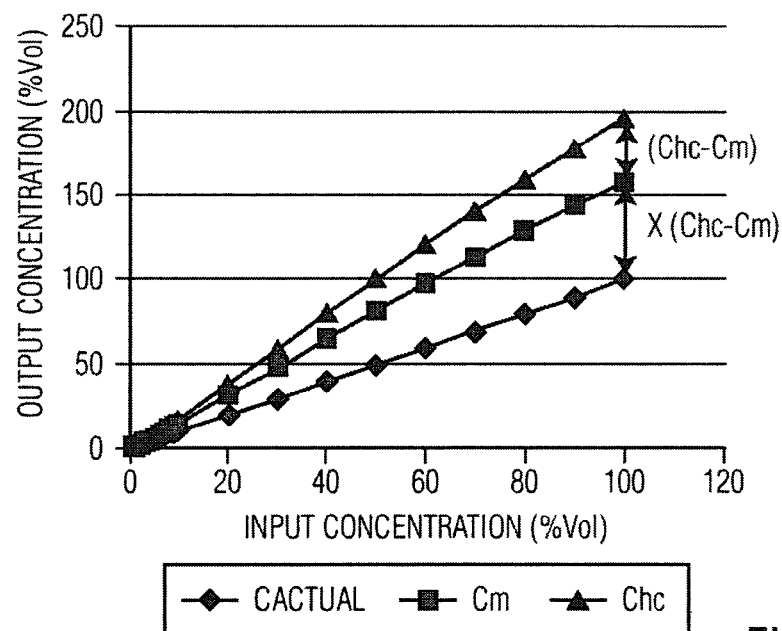
FIG. 7 is a graph showing lineariser response to natural gas using the correction algorithm of the invention.

To rectify this, the preferred embodiment of the method of the invention uses equation 19 (also see FIG. 7), to combine the two channels to estimate the actual concentration of gas being measured.

$$c_{actual} = c_1 - X \cdot (c_2 - c_1) \quad (19)$$

Figure 6:
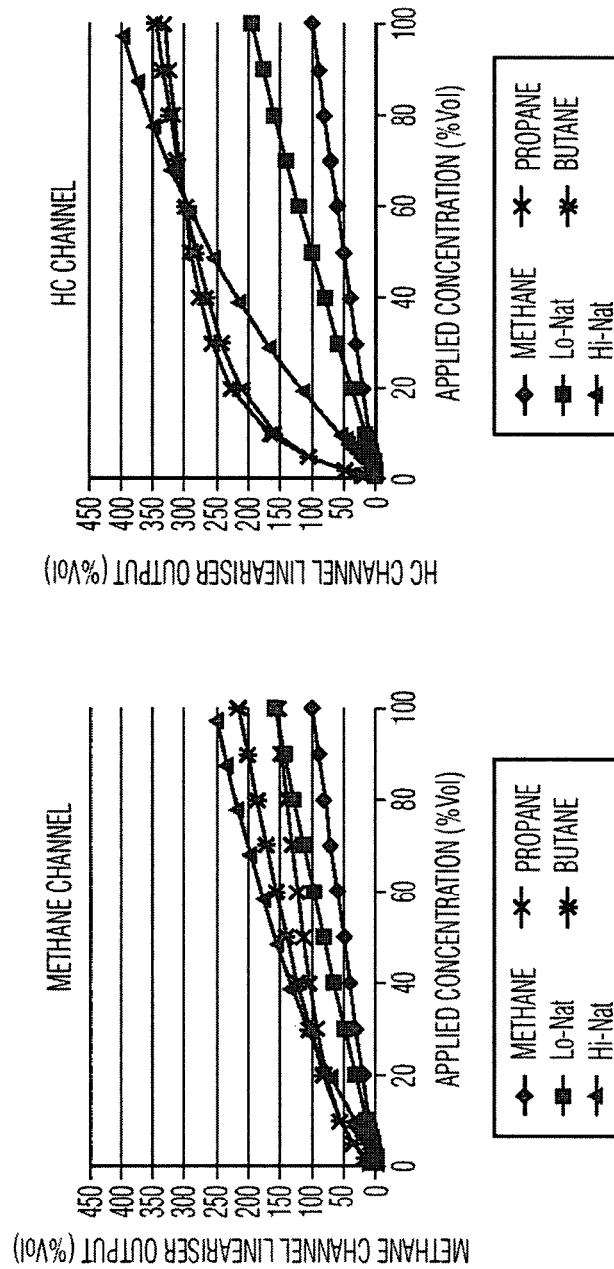
FIG. 6 are graphs showing methane and hydrocarbon sensor lineariser output incorporating the method of the invention for different gases.
Figure 8:
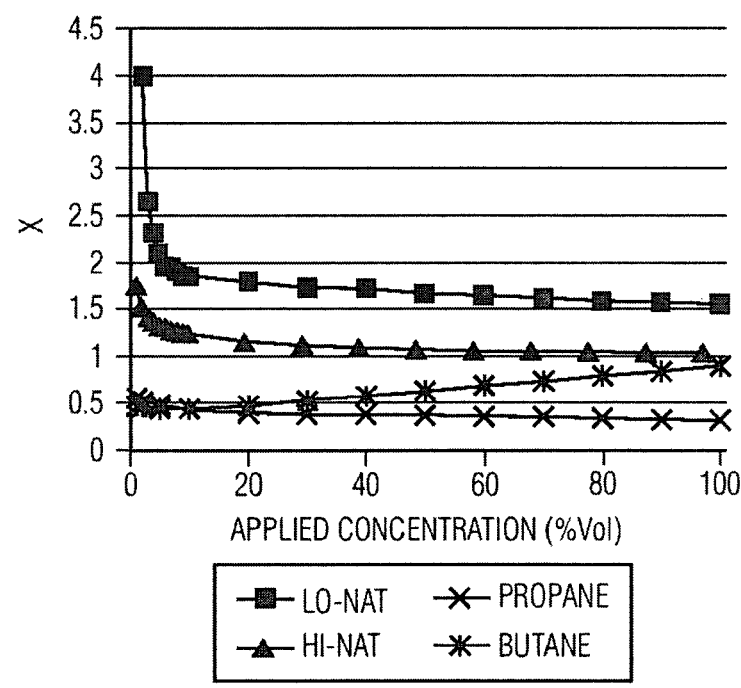
FIG. 8 is a graph showing variation in algorithm correction factor for different gases.

From the data shown in FIG. 6 is used to calculate the correction factor 'X' for each gas, as shown in FIG. 8.

$$X = \frac{c_1 - c_{actual}}{c_2 - c_1} \quad (20)$$

Figure 9:
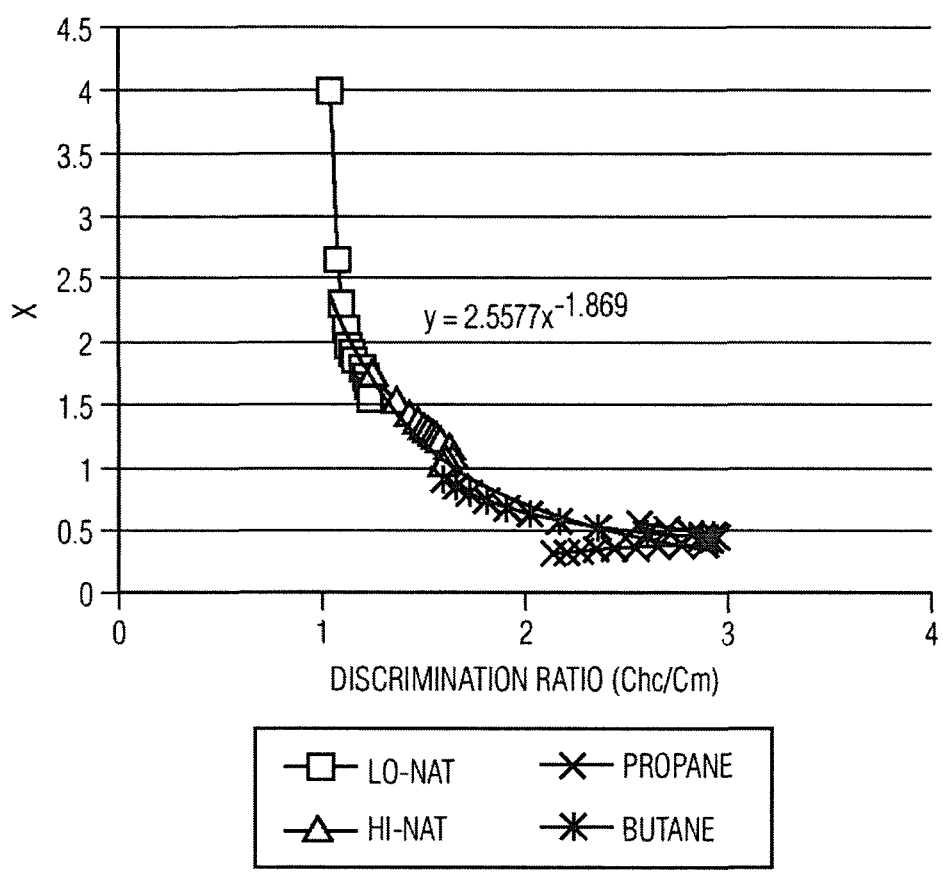
FIG. 9 is a graph showing variation in algorithm correction factor with discrimination ratio.

FIG. 8 shows that each gas type has its own profile for the correction factor 'X'. When 'X' is plotted against the Discrimination Ratio there appears to be a trend relating the two values, as illustrated in FIG. 9.

Therefore the correction factor 'X' can be calculated using the equation, $$X = 2.5577 \cdot \left(\frac{c_1}{c_2}\right)^{1.869} \quad (21)$$

While this correction factor works reasonably well for natural gas, it does not as well for the propane and butane. However, if the instrument is intended for propane or butane measurement it would be calibrated as such. This method ensures that the instrument will give a sensible reading regardless of the gas being detected. The natural gas discrimination sensor is only intended to give a 'YES/NO' decision on whether the gas is methane or not. It is not intended to be a completely accurate measurement tool for all gases at all times.

Figure 10:
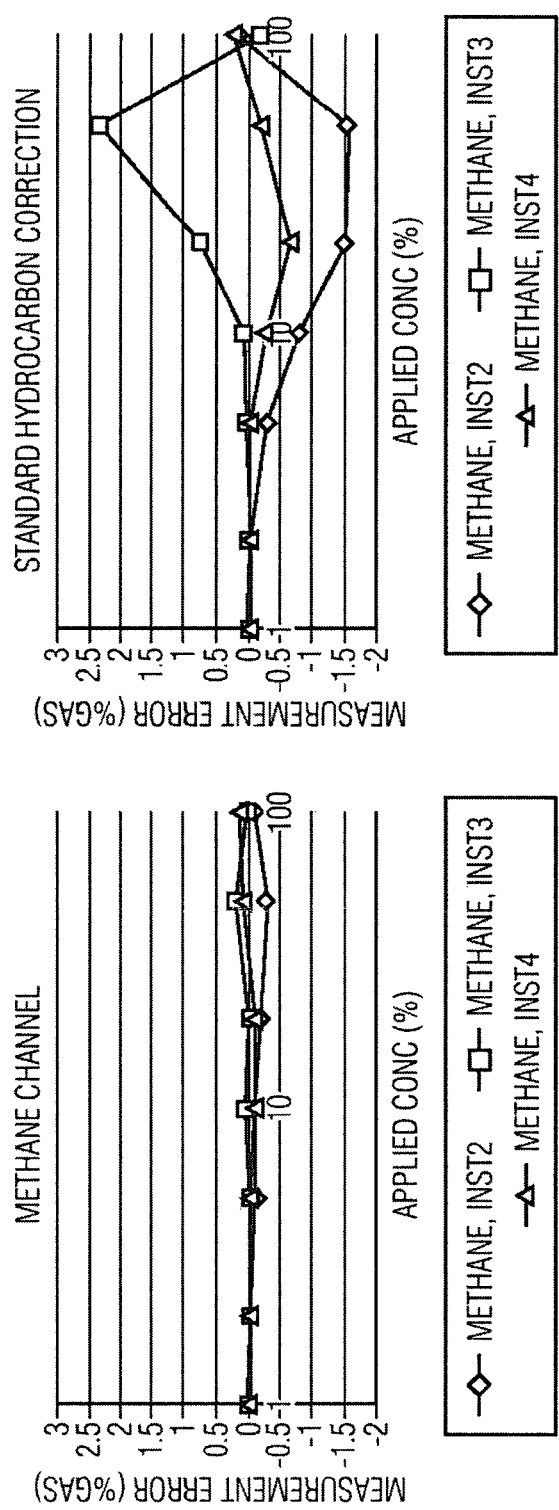
FIG. 10 are graphs showing the measurement error in a methane sensor compared to the error created by the hydrocarbon correction algorithm for methane according to the invention.

With the hydrocarbon correction algorithm in place it can introduce noise to the measurement when recording methane. FIG. 10 shows that while there is very little noise on the single methane channel, the hydrocarbon correction algorithm appears to amplify any measurement error.

To counteract this effect the correction algorithm is applied only if natural gas is detected. If the gas is methane, then only the methane channel output should be used as the displayed measurement. To enable a smooth transition between using a single channel to switching to a combination of both measurement channels a set of switching limits is used.

To achieve this equation 19 is modified to be, $$c = M2 \cdot (c_1 - X \cdot (c_2 - c_1)) + M1 \cdot c1 \quad (22)$$

The limits and conditions for the calculation of M1 and M2 are as follows,
('if' statements are written in Microsoft Excel™ syntax)

$$Z = \text{if}\left(\frac{c_1}{c_2} < 0.9, 0.9, \text{if}\left(\frac{c_1}{c_2} > 1, 1, \frac{c_1}{c_2}\right)\right) \quad (23)$$

$$M1 = \frac{Z - 0.9}{1 - 0.9} \quad (24)$$

$$M2 = \frac{1 - Z}{1 - 0.9} \quad (25)$$

Equation 22 effectively means that if the gas being measured is methane, $$c = c_1$$

If the gas being measured is natural gas then, $$c = c_1 - X \cdot (c_2 - c_1)$$

So the problems with noise being added to the methane measurement go away.

To simplify the software needed to implement the hydrocarbon correction algorithm, rather than compute 'X', a look up table can be used to replicate equation 21. This can be taken a step further and a look up table created for equation 22 based on the equation, $$X1 = \frac{c_1 - c_{eq22}}{c_2 - c_1} \quad (26)$$

Figure 11:
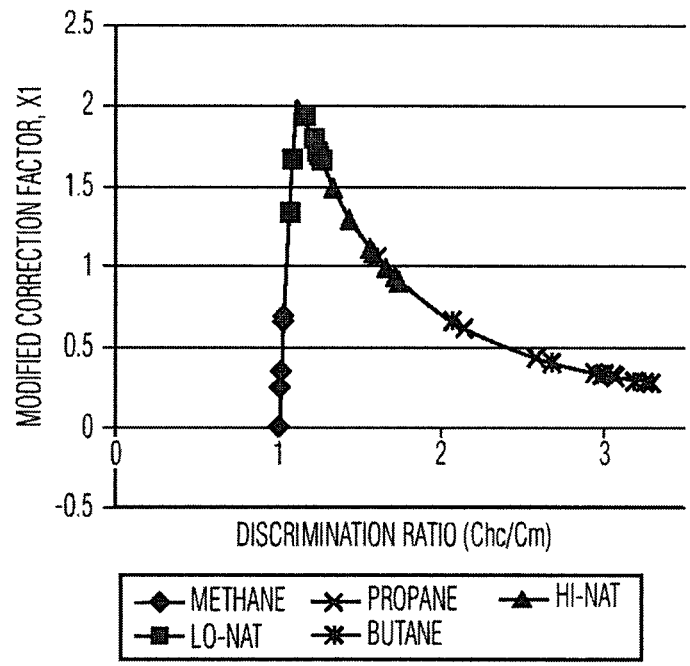
FIG. 11 is a graph showing the variation of a modified correction factor with discrimination ratio.

This produces the data shown in FIG. 11.
Therefore, equation 22 can be replaced by, $$c = c_1 - X1 \cdot (c_2 - c_1) \quad (27)$$

The method of the invention and associated detector enables measurement of the concentration of a detectable gas, namely methane, and the discrimination of methane from natural gas (and other hydrocarbons). The detector houses at least three individual pyroelectric detectors, each with a different spectral filter attached. The first detector is for detecting primarily methane, the second is for detecting the higher hydrocarbons and the third is used as a reference.

The preferred filter specs are:
Filter 1 (methane): 3.33 um+/−0.1 um
Filter 2 (higher hydrocarbons): 3.40 um+/−0.1 um
Filter 3 (reference): 3.95 um+/−0.1 um The bandwidth of each filter is in the order or hundreds of nanometers, such as, for example, 160 nm for Filter 1, 120 nm for Filter 2, and 90 nm for Filter 3. These bandwidths values are not, however exclusive, and will vary depending on the specification of the sensors used.

The combination of the methane detector and reference detector, and hydrocarbon detector and reference detector serve to create a methane channel and hydrocarbon channel respectively. By creating methane linearisers for each channel, and monitoring the ratio of the concentrations measured by the two channels, we can set limits on to enable the identification of the gas type being monitored.

The preferred limits are, $$R = \frac{c_2}{c_1}$$

If $C_1 < Y$, then gas is undermined; (Levels are too low to make a reliable decision)
If $C_1 > Y$ AND $R < 1.025$, then gas is methane;
If $C_1 > Y$ AND $1.025 < R < 1.05$, then gas is undetermined; (this is a buffer to take into account noise and sensor to sensor variation in linearity)
If $C_1 > Y$ AND $R > 1.05$, then gas is natural gas;
where Y is a constant which is selected to provide acceptable results depending on the particular calibration value etc. Preferably, Y is less than or equal to 1.5, and more particularly is equal to 1.0, especially for calibration at 1% concentration of methane.

Figure 12:
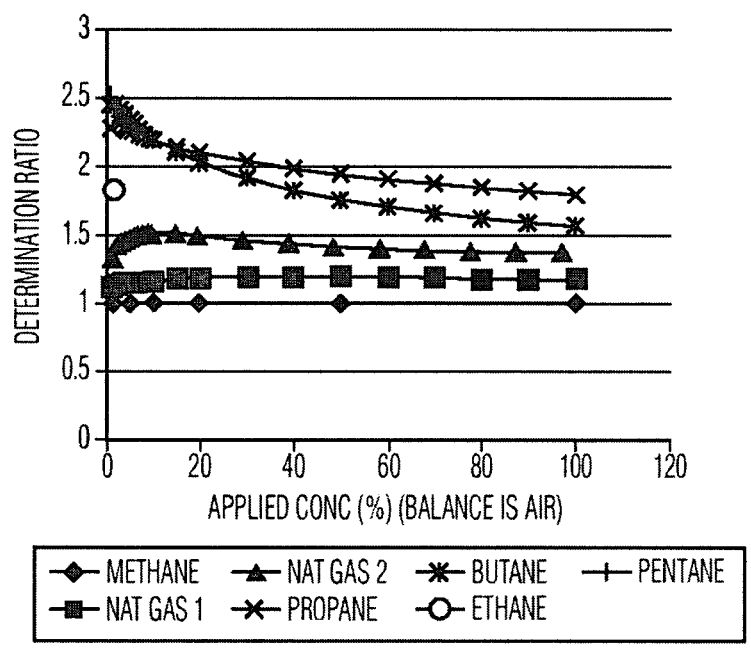
FIG. 12 is a graph showing the variation of determination ratio with concentration for different gases for detector utilising the method of the invention.

Referring now to FIG. 12, this shows how the gas determination ratio (R) varies for different gas mixtures for the detector incorporating the sensor arrangement of the invention. This suggests that if R is greater than or equal to 2, then it is likely propane/butane (the two are indistinguishable), aka LPG is present. However, it does not follow, based just on this information, that if R is less than 2 then the gas is Natural gas, because for high concentrations of gas, the data shows that the ratio for LPG drops below 2. Accordingly, the invention may be used to detect the presence of LPG by applying a different algorithm according to which, if $R \geq 2$, then the gas is LPG, and if $R < 2$ and the concentration is determined to be less than a defined figure (from FIG. 12, less than 20% and more particularly less than 10% to allow for variations in sensors readings between detectors), then the gas is not LPG.

Issues with linearity due to sensor to sensor variation are minimised by implementing a three point calibration. The sensor is calibrated preferably at 100%, 5% and 1% methane. The calibration at 1% and 5% methane need only be a one off for each sensor.

The method of the invention also provides an estimated indication of gas concentration if the gas being detected is natural gas. The linearisers for methane will give a high reading if natural gas is detected. This method ensures that the instrument does not produce unrealistic readings in the presence of natural gas or higher hydrocarbons.

Whilst it has been found that the use of equation 19 above with $X = A \cdot (c_1/c_2)^B$, where A and B are constants for a particular pair of filter wavelengths chosen depending on the gases which are being looked for in the sample produces satisfactory results in many applications, the accuracy of the corrected concentration derived using that equation is found to diminish with some sensors. According to a further development of the invention, then, it has been found that accuracy of the concentration reading can be further improved by modifying the value of X using a variable multiplier D, the value of which depends upon the composition of the gas being measured.

In particular, it has been found that the value of the constant A calculated as set out above is necessarily constant for a given sensor used with a given gas, but may vary depending on the particular composition of the gas being sampled. In a further embodiment of the invention, therefore, improved values can therefore be obtained if the constant A is modified by the new variable D, dependent on the actual concentration readings taken from the two sensors, such that X in equation 19 becomes:

$$X = D \cdot A \cdot (c_1/c_2)^B \quad (28)$$

In this alternative embodiment, which improves accuracy over a range of natural gas compositions and of concentrations, a detector is first calibrated by taking concentration readings for two natural gas mixtures, NG1 and NG2 These can be any two mixtures but in order to get better accuracy across the range, it is preferred that they represent extremes of the compositions which might be analysed by the detector in practice. To that end, it has been found to work well if the compositions are as follows:

- NG1 being a mixture composed mainly of methane, with the minimum addition of higher hydrocarbons which is expected to be found in use. IN this example, a mixture of 98% Methane and 2% Ethane is used but other composition is possible as long as the actual composition is known.
- NG2 is similar, but with the maximum extra higher hydrocarbons expected to be found in use. In this example, a mixture of 90% Methane and 10% Ethane is used, but again, other composition is possible as long as the actual composition is known.

It will also be recognized that more than two known compositions can be used if required, for example if greater accuracy is needed.

Measurements, preferably at least two, are taken on the detector for each gas mixture—one at 50% mix of the gas with another gas, for example Nitrogen, and one at 100% of the natural gas mixture (NG1 or NG2), each measurement giving a reading for each sensor ($c_1$ and $c_2$)

Nitrogen is preferred as the other gas as it reduces the risk of explosion but other gases could also be used, such as air.

Furthermore, more than two measurements can be taken for each gas mixture without departing from the scope of the invention, each being taken at different mixture compositions with another gas. Two measurements are preferred as this is found to give a good level of accuracy without making the calibration process too arduous and time consuming. However, if greater accuracy is requirement, more than two sets of measurements can be taken.

FIG. 13 shows an illustrative graph of example data produced by the example, with Methane sensor output reading ($c_1$) being plotted against the ratio of the two sensor output readings ($c_2/c_1$). The x-axis is the % methane equivalent, so when tested in 50% and 100% methane, the ratio is 1. When tested in either concentration of NG1, the ratio is higher, and in NG2 higher still; as is the % methane equivalent reading.

This analysis gives four sets of data, two for NG1 (one for 50% concentration and one for 100% concentration), and two for NG2 (at 50% and 100% concentration). Each set of data comprises a value for C1, a value for C2 and a value for the actual concentration Ccor, which is known because the compositions of NG1 and NG2 are known.

Combining equations 19 and 28, and rearranging for D, D is then given as:

$$D = \frac{c_1 - c_{cor}}{A \cdot (c_1/c_2)^B (c_2 - c_1)} \quad (29)$$

Values of A and B are know from the first embodiment described above, and the values of C1, C2 and Ccor obtained by the four sets of data can be used to generate four values for D, two for NG1 and two for NG2. These can be plotted on a graph as shown in FIG. 14 with the coefficient D on the y-axis, and the methane sensor output value (C1) on the X-axis.

A straight line approximation for the relations between C1 and D2 for a particular composition has been found to be a good approximation, and hence the data, as displayed in FIG. 14, is used to generation a linear equations between C1 and D for each of NG1 ($D_{NG1}$) and NG2. ($D_{NG2}$)

The data is then further extrapolated between the two linear approximations for concentrations which are neither NG1 nor NG2. If the measured ratio is below the ratio for NG1, the value is interpolate between the line for NG1 and the line for methane (correction factor=1). If the measured ratio is between NG1 and NG2, the value is interpolate between the line for NG1 and the line for NG2. If the ratio is higher still, the line for NG2 is used.

The actual correction factor, D, which should be applied for a particular composition being analysed, is calculated in the instrument using the equations below, $$D = NG1_{cor} \cdot D_{NG1}(c_1) NG2_{cor} \cdot D_{NG2}(c_1) \quad (30)$$

Equation 30 relates the measurement values from an unknown gas mixture to the know values shown in FIGS. 13 and 14. The correction factors $NG1_{cor}$ and $NG2_{cor}$ determine the position of the measured determination ratio to the known determination ratio values at 100% NG1 and NG2, and are calculated using, $$NG1_{cor} = \frac{R_{@100\%NG2} - R}{R_{@100\%NG2} - R_{@100\%NG1}} \quad (31)$$

$$NG2_{cor} = \frac{R - R_{@100\%NG1}}{R_{@100\%NG2} - R_{@100\%NG1}} \quad (32)$$

Where the determination ratio $R = C_2/C_1$, and $R_{@100\% \; NG1}$=Determination ratio at 100% NG1, $R_{@100\% \; NG2}$=Determination ratio at 100% NG2.

$D_{NG1}$ and $D_{NG2}$ are the equations shown in FIG. 14.

Each detector is therefore calibrated using this processes and the processor is programmed with values for $R_{@100\% \; NG1}$, $R_{@100\% \; NG2}$, as well as the characteristic equations $D_{NG1}$ and $D_{NG2}$ derived for that detector during the calibration procedure. The values for C1 and C2 obtained for the sample being analysed are then used in equation 30 to generate a value for D, which in turn is used in Equation 28 and equation 19 to generate a corrected value for the actual concentration of the sample.

EXAMPLE 1

As an example, using the above graphs, if the methane reading is 100 and the ratio is 1.1 (graph 1), the ratio for NG1 is approximately 1.2, so a line midway between the methane line (y1) and the NG1 line ($D_{NG1}$=−0.0003729x+ 1.1014806) is used. This gives a correction factor of approximately 1.025. The calculation is shown in broken line on FIG. 14.

EXAMPLE 2

If the methane sensor gives a reading of 80 and the ratio is 1.3, i.e. the correction factor lies between NG1 and NG2, then from FIG. 13, the ratio for 100% NG1 is 1.2 and the ratio for 100% NG2 is 1.45. Therefore (1.45−1.3)/(1.45−1.2) of the correction factor for NG1 and (1.3−1.2)/(1.45−1.2) of the correction factor for NG2 is used. This gives a figure of 0.6× the correction factor for NG1 and 0.4× the correction factor for NG2.

The reading from the methane sensor are then used in the equation for NG1 and NG2, i.e.

$D_{NG1}$: −0.0003729×80+1.1014806=1.072

$D_{NG2}$: −0.0003773×80+1.2146882=1.185

The final correction factor (D) in this example if then given by 0.6×1.072+0.4×1.185=1.1172. This figure can be confirmed from Graph 2.

It will, of course, be understood that while the various parts and features of the method have been described in combination, the advantages afforded by different parts of the method may be achieved in isolation of each other, at least in part, and the description of the whole method is not in any way meant to restrict the teaching of the application only to the use of the different aspects in combination with each other. Equally, although the method has been described primarily in connection with the detection of methane and natural gas, other gas combinations are also possible.

The invention claimed is:

1. A method of measuring the concentration of a first gas in a sample, the method comprising:
   providing a detector having a sensor responsive to a first wavelength, a sensor responsive to a second wavelength, and a sensor for taking reference readings;
   applying a lineariser function to each of the first and second absorption figures to calculate first and second concentration figures;
   calibrating the sensor for each wavelength for detecting the first gas such that the data at each wavelength gives the same reading when only the first gas is present in a sample;
   analysing a gas sample to obtain a first absorption reading at the first wavelength, a second absorption reading at the second wavelength and a reference reading;
   calculating a first concentration figure ($c_1$) and a second concentration figure ($c_2$) using the reading at the first wavelength, the reading at the second wavelength and the reference reading; and
   calculating a corrected concentration figure ($c_{cor}$) indicative of the actual concentration of the first gas in the sample using the equation $c_{cor}=c_1-X \cdot (c_2-c_1)$, in which $X=D \cdot A \cdot (c_1/c_2)^B$, where A and B are constants for a particular pair of filter wavelengths chosen depending on the gases which are being looked for in the sample, and D is a correction factor which depends on concentration of the first gas in the sample.

2. The method according to claim 1, wherein the value of D is extrapolated from calibration readings taken using the detector to measure the concentration of at least a first gas mixture of known composition at least at two known concentrations, and a second gas mixture of a known composition which is different to the composition of the first gas mixture at least at two known concentrations.

3. The method according to claim 2, wherein the calibration readings are taken using the same concentration values for each of the first and second gas mixtures.

4. The method according to claim 3, wherein the other concentrations is 50% of the gas mixture mixed with another gas.

5. The method according to claim 2, wherein one of the known concentrations is 100% of the first gas mixture, and 100% of the second gas mixture.

6. The method according to claim 5, wherein the other gas is nitrogen.

7. The method according to claim 2 wherein calibration values of D are calculated using readings taken from sample of known composition using the equation $$D = \frac{c_1 - c_{cor}}{A \cdot \left(\frac{c_1}{c_2}\right)^B (c_2 - c_1)}$$

where $C_1$ and $C_2$ are the sensor readings take for the sample and $C_{cor}$ is the actual concentration of the gas in the known sample.

8. The method according to claim 2, wherein the value of D for a sample of unknown composition is extrapolated from the calibration values of D using a linear extrapolation between the calibration values to extrapolate to a value of D for the measured value of C1 for the sample.

9. The method according to claim 8, wherein D is calculated for a particular sample of unknown composition using the equation:

$$D = NG1_{cor} \cdot Y_{NG1}(c_1) + NG2_{cor} \cdot Y_{NG2}(c_1)$$

where $$NG1_{cor} = \frac{R_{@100\%NG2} - R}{R_{@100\%NG2} - R_{@100\%NG1}}$$

and $$NG2_{cor} = \frac{R - R_{@100\%NG1}}{R_{@100\%NG2} - R_{@100\%NG1}}$$

With $R=c_2/c_1$; $R_{@100\%NG1}$=calibration Determination ratio measured at the at least one known concentration of the first gas mixture of known composition NG1, $R_{@100\%NG2}$=calibration Determination ratio measured at the at least one known concentration of the second gas mixture of known composition NG2, and $D_{NG1}$ is the linear equation which extrapolates between the calibrations values of D for the first gas mixture and $D_{NG2}$ is the linear equation which extrapolates between the calibrations values of D for the second gas mixture.

10. The method according to claim 1, wherein the first gas is methane and its concentration is being measured in a sample containing natural gas or another higher hydrocarbon.

11. The method according to claim 10, wherein A=2.5577 and B=1.869.

12. The method according to claim 1, wherein in the event that the gas present is methane, the output of the sensor responsive to the first wavelength only is used to calculate the concentration reading.

13. A method according to claim 1, wherein the equation is used only where the ratio of the reading of the sensor responsive to the first wavelength to the sensor responsive to the second wavelength ($c_1/c_2$) is above a first threshold value, the output of the sensor responsive to the first wavelength only is used where ($c_1/c_2$) is below a second threshold value, and a transitioning algorithm is used where ($c_1/c_2$) is between the first and second threshold values.

14. The method according to claim 13, wherein the first threshold value is 1, and the second threshold value is 0.9.

15. The method according to claim 14, wherein the correction equation is $c_{cor}=M_2 \cdot (c_1-X \cdot (c_2-c_1))+M1 \cdot c_1$, where $M1=(z-0.9)/(1-0.9)$, and $M2=(1-z)/(1-0.9)$, with $z=0.9$ when $(c_1/c_2)<0.9$, $z=1$ when $(c_1/c_2)>1$, and $z=(c_1/c_2)$ when $0.9 \leq (c_1/c_2) \leq 1$.

16. A method of measuring the concentration of a first gas in a sample, the method comprising:
   providing a detector having a sensor responsive to a first wavelength, a sensor responsive to a second wavelength, and a sensor for taking reference readings;
   applying a lineariser function to each of the first and second absorption figures to calculate first and second concentration figures;
   calibrating the sensor for each wavelength for detecting the first gas such that the data at each wavelength gives the same reading when only the first gas is present in a sample;
   analysing a gas sample to obtain a first absorption reading at the first wavelength, a second absorption reading at the second wavelength and a reference reading; and
   calculating a first concentration figure ($c_1$) and a second concentration figure ($c_2$) using the reading at the first wavelength, the reading at the second wavelength and the reference reading, and calculating a corrected concentration figure ($c_{cor}$) indicative of the actual concentration of the first gas in the sample using the equation $c_{cor}=c_1-X \cdot (c_2-c_1)$, in which $X=A \cdot (c_1/c_2)^B$, where A and B are constants for a particular pair of filter wavelengths chosen depending on the gases which are being looked for in the sample.

17. A method of identifying the presence of a first gas within a sample, the method comprising:
   providing a detector having a sensor responsive to a first wavelength, a sensor responsive to a second wavelength, and a sensor for collecting reference readings;
   analysing a gas sample to obtain a first absorption reading corresponding to the first wavelength, a second absorption reading corresponding to the second wavelength and a reference reading;
   calculating a first absorption figure using the first absorption reading and the reference reading, and a second absorption figure using the second absorption reading and the reference reading;
   applying a lineariser function to each of the first and second absorption figures to calculate first and second concentration figures;
   calibrating the sensor for each wavelength for detecting the first gas such that the data collected at each wavelength gives the same reading when only the first gas is present in a sample; and
   calculating the ratio of the first concentration figure to the second concentration figure, and using the ratio to identify whether only the first gas is present in the sample.

18. The method according to claim 17, wherein the first gas is methane and the sample includes higher hydrocarbons such as propane and butane mixed with methane.

19. The method according to claim 17, wherein the first wavelength is 3.3 microns plus or minus 0.1 microns and the second wavelength is 3.4 microns plus or minus 0.1 microns.

20. The method according to claim 19, wherein the step of calibrating the sensors comprises calibrating the sensors for detecting methane such that the same reading is obtained at each wavelength when analysing a sample containing methane but no other hydrocarbons.

21. The method according to claim 17, wherein compensation is carried out separately on the reading at each wavelength in order to eliminate errors due to variations in environmental parameters.

22. The method according to claim 21, wherein at least one of temperature compensation and pressure compensation is carried out.

23. The method according to claim 22, wherein temperature compensation is carried out in two stages including zero drift correction and span drift correction.

24. The method according to claim 17, wherein the sensor responsive to the first wavelength is a first sensor and the sensor responsive to the second wavelength is a second sensor distinct from the first sensor.

25. The method according to claim 17, wherein a single sensor operable in different modes is used to analyse the gas sample to obtain absorption readings corresponding to both the first and second wavelengths.

26. The method according to claim 17, wherein at least one of the sensor responsive to the first wavelength, the sensor responsive to the second wavelength, and the sensor for collecting reference readings is an infrared radiation absorption sensor.

27. A selective gas detecting apparatus according to claim 17, wherein at least one of the sensor responsive to the first wavelength, the sensor responsive to the second wavelength, and the sensor for collecting reference readings is an infrared radiation absorption sensor.

28. A selective gas detecting apparatus comprising:
   a sensor responsive to a first wavelength;
   a sensor responsive to a second wavelength, and;
   a sensor for collecting reference readings; and
   a processor, the processor being configured to:
      calculate a first absorption figure using the reading for the first wavelength and the reference reading, and a second absorption figure using the reading for the second wavelength and the reference reading;
      calculate first and second concentration figures by applying a lineariser function to each of the first and second absorption readings, the sensor for each wavelength being calibrated for detecting the first gas such that the reading for each wavelength is the same when only the first gas is present in a sample;
      calculate the ratio of the first concentration figure to the second concentration figure; and
      identify the gas which is present in the sample based on the calculated ratio.

29. The selective gas detecting apparatus according to claim 28, wherein a separate sensor is used for each of the first wavelength, the second wavelength and the reference reading.

* * * * *

UNITED STATES PATENT AND TRADEMARK OFFICE
CERTIFICATE OF CORRECTION

PATENT NO. : 10,247,666 B2
APPLICATION NO. : 15/747516
DATED : April 2, 2019
INVENTOR(S) : Crawford Massie Page 1 of 1

It is certified that error appears in the above-identified patent and that said Letters Patent is hereby corrected as shown below:

In the Specification

Column 6
Lines 1-6, delete "one known concentration of the second gas mixture of known composition NG2, and DNG1 is the linear equation which extrapolates between the calibrations values of D for the first gas mixture and DNG2 is the linear equation which extrapolates between the calibrations values of D for the second gas mixture." and insert the same on Column 5, Line 67, as a Continuation of the same Paragraph.

Column 11
Line 13, delete "ExcelTM" and insert -- Excel(RTM) --, therefor.

Column 14
Line 21, delete "D=NG1cor.DNG1(c1)NG2cor.DNG2(c1)" and insert
-- D=NG1cor.DNG1(c1)+NG2cor.DNG2(c1) --, therefor.

In the Claims

Column 18
Line 36, in Claim 28, delete "wavelength, and;" and insert -- wavelength; --, therefor.

Signed and Sealed this
Ninth Day of July, 2019

Andrei Iancu
*Director of the United States Patent and Trademark Office*